United States Patent [19]

Bohn et al.

[11] 4,297,274

[45] Oct. 27, 1981

[54] PROTEIN FROM RED BLOOD CELLS AND PROCESS FOR ISOLATING IT

[75] Inventors: Hans Bohn; Heinz Haupt, both of Marburg an der Lahn, Fed. Rep. of Germany

[73] Assignee: Behringwerke Aktiengesellschaft, Marburg an der Lahn, Fed. Rep. of Germany

[21] Appl. No.: 128,253

[22] Filed: Mar. 7, 1980

Related U.S. Application Data

[63] Continuation of Ser. No. 898,519, Apr. 20, 1978, abandoned.

[30] Foreign Application Priority Data

Apr. 25, 1977 [DE] Fed. Rep. of Germany ....... 2718326

[51] Int. Cl.$^3$ ................................................ C07G 7/00
[52] U.S. Cl. ........................... 260/112 B; 260/112 R; 424/101; 424/105; 424/177; 424/85; 424/88
[58] Field of Search ....................... 260/112 B, 112 R; 425/101, 105, 177, 85, 88

[56] References Cited

U.S. PATENT DOCUMENTS

| | | | |
|---|---|---|---|
| 3,904,751 | 9/1975 | Zwisler et al. | 424/105 |
| 3,910,822 | 10/1975 | Pentchev et al. | 424/105 X |
| 3,931,399 | 1/1976 | Bohn et al. | 424/105 |
| 4,018,885 | 4/1977 | Bohn et al. | 260/112 B |
| 4,041,021 | 8/1977 | Bohn | 260/112 B |
| 4,065,445 | 12/1977 | Bohn et al. | 260/112 B |

OTHER PUBLICATIONS

Centonze et al., Chem. Abstracts, vol. 55:23,724f (1961).
Bohn et al., Chem. Abstracts, vol. 77:118,184f, 162,901m (1972).
Bohn, Chem. Abstracts, vol. 83:92,637c (1975).
Bohn et al., Chem. Abstracts, vol. 76:23,468s (1972).
Bohn et al., Chem. Abstracts, vol. 85:88,842q (1976).
Bohn, Chem. Abstracts, vol. 80, 1974, 25865a.

Primary Examiner—Howard E. Schain
Attorney, Agent, or Firm—Curtis, Morris & Safford

[57] ABSTRACT

The invention relates to a new protein which can be immunologically proved in the lysate of human erythrocytes and isolated therefrom and which has the following properties:

- a protein proportion of 99%±1%, preponderantly consisting of α-amino-acids,
- a carbohydrate proportion of 0.9%±0.5%,
- a sedimentation coefficient of $S_{20,w}^{C=0}$ of 6.88±0.50 S,
- a molecular weight of 160,000±15,000,
- an iso-electric point of 5.5±0.2,
- an electrophoretic mobility in the range of the $\beta_1$-globulins of the human serum, and
- a specific immunological reaction with an antibody directed specifically against the protein;

and a process for isolating it. The new protein is suitable as diagnostic agent and for the preparation of antisera.

8 Claims, No Drawings

PROTEIN FROM RED BLOOD CELLS AND PROCESS FOR ISOLATING IT

This is a continuation of application Ser. No. 898,519, filed Apr. 20, 1978, now abandoned.

The present invention relates to a new protein which can be immunologically proved in the lysate of human erythrocytes and isolated therefrom and to a process for its isolation.

It is known that the lysate of human erythrocytes contains, in addition to its main constituent, i.e. the hemoglobin, a great number of enzymes the enzyme activity of which has been well and thoroughly investigated. Among those are carboanhydrase B, carboanhydrase C, superoxide-dismutase, catalase, lactate dehydrogenase, glutathione-reductase, acidic phosphatase, glucose-6-phosphate-dehydrogenase, 6-phosphoglutonate-dehydrogenase, glucose-6-phosphatisomerase, phosphoglucomutase, phospho-glycerate kinase, adenylate kinase, as well as a protein which combines in itself the three enzyme activities 2,3-di-phosphoglycerate mutase, 2,3-di-phosphoglycerate phosphatase and phosphoglycero-metase. Some of them have been isolated.

Now, we have found a new protein which differs from the known proteins by its physical-chemical and immunological properties and also by its quantitative occurrence in the hemolysate.

Thus, the object of the invention is a new protein which is characterized by:
- a protein proportion of 99%±1%, essentially consisting of α-amino-acids,
- a carbohydrate proportion of 0.98%±0.5%,
- a sedimentation coefficient $S_{20w}^{C=O}$ of 6.88±0.50 S,
- a molecular weight of 160,000±15,000,
- an isoelectric point of 5.5±0.2,
- an electrophoretic mobility in the range of the $\beta_1$-globulins of the human serum, and
- a specific immunological reaction with an antibody specifically directed against the protein.

Owing to the most outstanding property of the protein, i.e. its molecular size and mobility, it can be designated as 7 S-$\beta_1$-globulin.

A remarkable feature of the new protein is that it can be proved immunologically in a stroma-free lysate of human erythrocytes and therein amounts to about 1% of the protein proportion, relative to the cell content of red blood corpuscles. With relation to hemoglobin and to carbonanhydrase B, the new protein is at the third greatest in quantity.

The following description shall serve to illustrate the characteristic features of the protein.

Determination of the sedimentation coefficient is carried out in an analytical ultracentrifuge at 56,000 rev./min. in double sector cells in a superposing cell as described by Vinograd, Proc. Acad. Sci. USA, 49, 902 (1963). The band which is absorbing at 280 nm and migrates in the superposition cell is measured. Distilled water having a pH-value of 7.0 is used as the solvent. The protein concentration is 10, 7.5 and 2.5 mg/100 ml solution.

The molecular weight was calculated, on the one hand, in the ultracentrifuge via determination of the sedimentation equilibrium according to Yphantis. A value of 160,000±15,000 was found. On the other hand, determination of the protein in a 1% strength sodium-dodecyl sulfate-containing carrier gel, consisting of polyacrylamide with humane placenta lactogen and human albumine as reference substances, yielded a molecular weight of 45,000±5,000. Accordingly, it can be assumed that the molecule is built up from four equal or very similar subunits.

The molecular weight may also be determined with an aid of the analytical column chromatography with cross-linked dextran as the carrier, such as Sephadex ® G 150 of Messrs. Pharmacia. With 0.01 M phosphate buffer of pH 7.0 and human serum as the reference substance, the new protein is eluted with the immunoglobulin A and the $C_3$-component of the complement system. This corresponds to a molecular weight of about 160,000 to 180,000. If the elution buffer is combined with 1 M of NaCl, a substance with a molecular weight of about 40,000 is obtained. This corresponds to the electrophoretically determined molecular weight of the subunits of the new protein.

For determining the isoelectric point, the process of the isoelectric focusing was used while employing the devices and reagents marketed for this purpose by Messrs. LKB Stockholm.

The electrophoretic mobility was determined using cellulose acetate as carrier foil in a barbital-Na buffer having a pH-value of 8.6.

The carbohydrates were determined according to Schultze, H. E., Schmidtberger R., Haupt J.: Untersuchungenüber die gebundenen Kohlenhydrate in isolierten Glykoproteinen, Biochem. Z, 329, 490 (1958).

Amino-acid analysis was carried out according to Moore S., Spakman, D. H., Stein W. H.; Chromatography of amino acids on sulfonated polystyrene resins, Anal. Chem. 30, 1185 (1958), using a liquid chromatograph. It was found that aspartic acid and glutamic acid were the most frequently occurring α-amino acids in the peptide chain.

Immunological characterization of the substance is effected in the most simple way according to a known diffusion process in which the antigen, i.e. the new protein, and an antibody which is directed against the new protein, or a crude antiserum containing such antibodies, are allowed to diffuse against each other in a carrier medium, for example agar. If both reaction components meet in a favourable proportion, a visible precipitate is formed. In view of this finding it is will be understood by the expert that all immunological techniques for proving and determining the new protein as well as the antibodies directed against the new protein are applicable. The antiserum of high specificity against the new protein can be obtained according to known processes, for example by immunizing rabbits with the isolated protein over a period of time of several weeks using an immunological adjuvant, for example complete Freunds' adjuvant. The blood of the immunized animals is then withdrawn, the serum is separated therefrom and, if desired, the antibody-rich gamma-globulin fraction is isolated. With the aid of this serum—or antibody preparation, the new protein can also be isolated quantitatively, for example according to the electro-immune-assay described by Laurell, C. B., Analyst. Biochem, 15, 45 (1966).

The present invention furthermore provides processes for the isolation of the above-described protein, which are characterized by fractionating solutions containing said protein, preferably lysates of erythrocytes, on the basis of the following criteria:

The protein can be precipitated with the aid of neutral salts. With ammonium sulfate, which is usually employed for such precipitations, the protein is precipitated from its 1% strength aqueous solution at a concentration of between 1.5 and 2 moles/l in the a pH-range in proximity of the neutral point.

Furthermore, the protein can be precipitated with the aid of organic solvents, which are usually employed in protein chemistry, for example ethanol at a volume concentration of 10%, from an aqueous solution having a weakly acid pH-value, for example in a 0.04 molar acetate buffer having a pH of 5.5 at 0° C.

It has been found that the new protein is precipitated with the water-soluble organic bases of the acridine and quinoline series, which are usually employed in protein precipitation process. It is precipitated, for example with 2-ethoxy-6,9-diaminoacridine lactate in a concentration of 0.01 mole/l at a pH % 8.0 from its aqueous solution.

The new protein can furthermore be precipitated with the organic acids usually employed in peptide chemistry for precipitations for example with trichloroacetic acid in a concentration of 0.2 mole/l and perchloric acid in a concentration of 0.6 mole/l.

Upon reduction of the electrical conductivity of the protein solution as can be obtained the removal of ions, the protein precipitates in the weakly acid range. Thus, precipitation of the protein is reached, for example, by dialysis against distilled water having a pH-value of 5.0.

The electrical properties of the protein make possible its fractionation with the aid of an ion exchanger. Basic anion-exchangers, in particular those containing diethylaminoethyl, triethylaminoethyl or quaternary bases or their derivatives as functional groups, bind the protein from a buffer solution which has a relatively low concentration. Adsorption can be prevented by increasing the salt concentration. On the other hand, there exists the possibility of adsorbing the protein and of eluting it again with the use of salt solutions having a higher concentration, or of buffer solutions having an elevated pH-value.

In view of the protein's electrophoretic mobility, preparative zone electrophoresis may be used advantageously for the enrichment or isolation of the protein. During electrophoresis the protein enriches in the β-range of the plasma-proteins and can then be isolated therefrom.

The immunological affinity of the protein for its antibodies may be employed for enriching the protein with the aid of the so-caled immuno-adsorption processes. For this purpose, an immuno-adsorbant, i.e. a carrier-bound antibody against the protein, may be prepared in a manner known per se which is capable of binding it specifically. The protein can then be eluted again by modification of the conditions of the medium.

Isolation of the substance of the invention by a selected combination of the afore-described methods which leads, on the one hand, to an enrichment of the protein, and, on the other hand, to its separation from the remaining accompanying proteins may also be carried out.

In addition to the possibilities shown here which provide the expert with the teaching of using the various methods of preparative protein chemistry for isolating the new protein, we now have found surprisingly a very simple process which is preferably used within the scope of the invention.

The new protein is adsorbed, at a low electrical conductivity of its aqueous solution between 1 and 10 $\mu$S/cm, preferably at between 2.5 and 2.8 $\mu$S/cm, on an anion exchanger, preferably a diethylaminoethyl ion exchanger, at a pH-value around the neutral point (pH 6.5–7.5). The charged adsorbent is separated from the remaining solution, suitably in a column used for chromatography, and treated with a salt solution of rising concentration (linear salt gradient) and the eluate is collected in portions. The individual portions are analyzed immunochemically and those fractions which react with the antibodies directed against the new protein are collected. These salt solutions are neutral salt solutions and buffer solutions. The linear salt gradient for the elution rises from 10 $\mu$S/cm to about 100 mS/cm.

The knowledge of the molecular weight of the new protein makes it possible to employ then methods which lead to the isolation or enrichment of substances having a molecular weight of 150,000. The methods of gel-filtration or ultra-filtration are advantageously used for this purpose. The fraction obtained by ion exchange chromatography and which contains the new protein can be separated with particular advantage on a molecular sieve. The individual fractions obtained by the separation are collected and likewise analyzed immunochemically. Those fractions which contain to a large part only the new protein are isolated.

The product so obtained is suitably stored at temperatures of below 0° C.

As has already been described, the isolated protein migrates uniformly with a mobility which corresponds to that of the β-1-globulins of the human serum. If the polyacryloamide gel electrophoresis is used for characterizing the product, a heterogenicity of the product can be proved. Two bands are found in the gel. Closer investigation has shown that this heterogenicity is due to a dissociation of the protein during its preparation. This dissociation can be prevented by adding a proteinase inhibitor for example the trypsin-callicrein inhibitor isolated from the lungs of animals. In other words, this means that proteinases such as plasmin or callicrein provoke a modification of the native protein. Such a modification is prevented by the addition of proteinase inhibitors. In electrolyte-free solution, the isolated protein shows a tendency to forming aggregates. These show in the ultracentrifuge a sedimentation coefficient of about 11.0S. The native component is reformed by increasing the salt concentration, for example to a value of 0.25 M/l of NaCl or phosphate. Further increase of the electrolyte concentration to anion strength of 0.5–1.0, for example by the addition of sodium chloride, leads to dissociations of the native molecule into sub-units with a sedimentation coefficient of about 3.0S. With an ion strength of $\mu=0.15$, the native molecule is reformed. On the other hand, the degree of dissociation is additionally dependent on the concentration of the total proteins of the solution. With a low protein concentration, for example <1%, the 3S-proportion is prevailing.

It is a feature of the present invention to add, during the isolation of the protein, a proteinase inhibitor, suitably a polyvalent proteinase inhibitor, in a quantity which is sufficient for the proteinase inhibition, to the aqueous solutions used.

The native molecule is most stable in salt solutions having ion strengths of from $\mu=0.01$ to $\mu=0.2$.

The starting material for the isolation of the new protein are red blood cells, erythrocytes. They are lyzed by introducing them into a hypotonic medium; the lysis is suitably effected with distilled water. In order to repel the proteolytic attack of enzymes present in the lysate, it is recommended to add a polyvalent proteinase inhibitor to the lytic agent, for example to the distilled water. The lysis is advantageously carried out at a weakly acid pH-value, for example at a pH-value between 5.5 and 6.0.

The particular components of the erythrocytes are separated from the so-called hemolysate after about 10 to 30 hours. It is advisable to use high speed centrifugation for this purpose; the stroma-free supernatatant obtained is then used for the preparation of the new protein. This solution can be treated with an ion exchanger and a molecular sieve as has already been described, whereafter the protein determined in the individual fractions by an identification method is further worked up or finally isolated.

Extracts from blood rich organs, for example from the placenta, are also suitable as starting materials for the isolation of the new protein.

The new protein can be obtained of course after what has been previously said here with the same purity also by combination of other steps under consideration of its precipitation properties.

The new protein is a valuable diagnostic agent. It is suitable in particular for the preparation of antisera according to the methods known for this purpose.

The invention is illustrated by the following Example.

EXAMPLE 2 l of packed red blood cells are washed three times each time with 2 l of physiological NaCl-solution. For hemolysis, 4 times the volume of distilled water is added. 10 mg of a proteinase inhibitor from bovine lungs (Antagosan ® of Behringwerke AG, Marburg) are added for each liter of hemolysate. The pH-value is adjusted to 5.8 with 1 N-acetic acid, while stirring. After standing overnight at 4°-6° C., the stroma which has flocculated out is removed by high speed centrifugation at 19,000 rpm. The pH-value is then adjusted to pH 6.8 with 1 N-sodium hydroxide solution. Thereafter, the electrical conductivity is 2.7 mS/cm.

1000 g (weight in the wet state) of diethylaminoethyl-cellulose in granular form is added to the stroma-free lysate and the whole is stirred intensively for 1 hour. Then, the adsorbant charged with protein is collected on a Buchner filter and washed until free from hemoglobin with 0.005 M of phosphate buffer, pH 6.8, which contains, per liter, 10 mg of the above-mentioned proteinase inhibitor. After introduction into a chromatography column, elution of the proteins is effected using a linear salt gradient of each time 5 liters of 0.005 M Na-phosphate buffer, pH 6.8, and 0.4 M of Na-phosphate buffer, pH 6.8, containing, per liter, 10 mg of Antagosan ®.

The eluate is collected in 500 ml portions.

Subsequently, characterization of the fractions is carried out by polyacryloamide gel electrophoresis. Those fractions which contain the main quantity of the 7S-$\beta_1$-globulin are mixed and concentrated by ultrafiltration. On the average, 40 ml of concentrate having a protein content of 5.5% are obtained.

For gel-filtration, the concentrate is introduced into a column filled with Sephadex ® G 150 (Pharmacia, Uppsala) which has been equilibrated with 0.01 M phosphate buffer, pH 7.0. The eluate is collected in 40 ml fractions which are characterized as above in the polyacryloamide gel electrophoresis. In the main peak the 7S-$\beta_1$-globulin is eluted. The fractions which seem pure are mixed and concentrated by ultra-filtration. The concentrate of the 7S-$\beta_1$-globulin is stored in a deep frozen state. The yield of protein from 2 liters of packed red blood corpuscles is on the average 1.5 g.

The product obtained shows the following composition of amino-acids and carbohydrates, error ranges due to analysis methods having to be taken into account:

| Amino-acids | Mol % | Variation coefficient % |
| --- | --- | --- |
| Lysine | 6.68 | 2.67 |
| Histidine | 1.61 | 5.08 |
| Arginine | 5.05 | 3.97 |
| Aspartic acid | 11.39 | 1.21 |
| Threonine | 5.05 | 2.23 |
| Serine | 4.98 | 4.12 |
| Glutamic acid | 8.44 | 4.35 |
| Proline | 5.66 | 6.95 |
| Glycine | 9.13 | 2.22 |
| Alanine | 7.35 | 1.68 |
| ½ Cystine | 1.65 | 2.04 |
| Valine | 8.96 | 1.36 |
| Methionine | 0.32 | 28.87 |
| Isoleucine | 4.84 | 1.17 |
| Leucine | 8.79 | 3.83 |
| Tyrosine | 3.34 | 4.24 |
| Phenylalanine | 5.92 | 3.81 |
| Tryptophan | 1.01 | 10.30 |

| Carbohydrates | % by weight |
| --- | --- |
| Hexoses (Gal/Man 1:1) | 0.9 ± 0.2 |
| Acetylhexoseamine | 0.3 ± 0.1 |
| Acetyl-neuraminic acid | 0 |
| Fucose | 0 |

We claim:

1. A process for isolating a protein characterized by
(a) a protein content of 99%±1% and a content of carbohydrates of 0.9%±0.5%, and a compositional analysis including the following major amino-acid and carbohydrate fractions:

| Amino Acids | Mol % | Variation Coefficient % |
| --- | --- | --- |
| Aspartic acid | 11.39 | 1.21 |
| Glutamic acid | 8.44 | 4.35 |
| Glycine | 9.13 | 2.22 |
| Alanine | 7.35 | 1.68 |
| Valine | 8.96 | 1.36 |
| Leucine | 8.79 | 3.83 |

| Carbohydrates | % by weight |
| --- | --- |
| Hexoses (Gal/Man 1:1) | 0.9 ± 0.2 |
| Acetylhexoseamine | 0.3 ± 0.1; |

(b) a sedimentation coefficient $S_{20w}^{C=0}$ of 6.88±0.5S;
(c) a molecular weight of 160,000±15,000;
(d) an iso-electric point of 5.5±0.2;
(e) an electrophoretic mobility in the range of the $\beta_1$-globulins of human serum; and
(f) a specific immunological reaction with an antibody specifically directed against the protein, which process comprises extracting the protein from red blood cells or from an aqueous solution having an electrical conductivity of from 1 to 10 μS/cm and containing the protein; adsorbing said protein from the aqueous solution on an anion exchanger at a pH value of between 6.5 and 7.5, thereby separating the protein from the supernatant of said aqueous solution; treating the anion exchanger and adsorbed protein with a series of salt solutions of varying concentration to elute that which was adsorbed on the exchanger in various fractions; identifying each fraction containing the protein; concentrating the protein by ultra-filtration; fractionating the concentrate by gel-filtration and elution; identifying each resultant fraction containing the protein, and concentrating the protein by ultra-filtration.

2. A process as defined in claim 1, wherein the red blood cells are lyzed by introducing them into a hypotonic medium and the sedimentary components of the red blood cells are removed to yield said aqueous solution containing the protein.

3. A process as defined in claim 1, wherein the protein is extracted from red blood cells in a blood-rich organ to form an aqueous solution containing the protein.

4. The process of claim 1, wherein a proteinase inhibitor is added to the aqueous solution containing the protein.

5. An isolated, concentrated, protein obtained by fractionating an extract of blood or of a blood-rich organ, said protein having
(a) a protein content of 99%±1% and a content of carbohydrates of 0.9%±0.5%, and a compositional analysis as follows:

| Amino Acids | Mol % | Variation Coefficient % |
|---|---|---|
| Lysine | 6.68 | 2.67 |
| Histidine | 1.61 | 5.08 |
| Arginine | 5.05 | 3.97 |
| Aspartic acid | 11.39 | 1.21 |
| Threonine | 5.05 | 2.23 |
| Serine | 4.98 | 4.12 |
| Glutamic acid | 8.44 | 4.35 |

-continued

| Amino Acids | Mol % | Variation Coefficient % |
|---|---|---|
| Proline | 5.66 | 6.95 |
| Glycine | 9.13 | 2.22 |
| Alanine | 7.35 | 1.68 |
| ½ Cystine | 1.65 | 2.04 |
| Valine | 8.96 | 1.36 |
| Methionine | 0.32 | 28.87 |
| Isoleucine | 4.84 | 1.17 |
| Leucine | 8.79 | 3.83 |
| Tyrosine | 3.34 | 4.24 |
| Phenylalanine | 5.92 | 3.81 |
| Tryptophan | 1.01 | 10.30 |

| Carbohydrates | % by weight |
|---|---|
| Hexoses (Gal/Man 1:1) | 0.9 ± 0.2 |
| Acetylhexoseamine | 0.3 ± 0.1 |
| Acetyl-neuraminic acid | 0 |
| Fucose | 0 |

(b) a sedimentation coefficient $S_{20w}^{C=O}$ of 6.88±0.5S;
(c) a molecular weight of 160,000±15,000;
(d) an iso-electric point of 5.5±0.2;
(e) an electrophoretic mobility in the range of the $\beta_1$-globulins of human serum; and
(f) a specific immunological reaction with an antibody specifically directed against the protein.

6. A process for the production of an antiserum to the protein defined in claim 5, which comprises immunizing a host vertebrate animal with said protein, withdrawing blood from the animal and separating the serum which contains antibodies to the protein from the blood.

7. The process as defined in claim 6, which further comprises isolating the gamma-globulin fraction, which contains said antibodies, from the serumm.

8. The antiserum which is the product of the process defined in claim 6 or 7.

* * * * *